(12) United States Patent
L'Alloret

(10) Patent No.: US 7,655,702 B2
(45) Date of Patent: *Feb. 2, 2010

(54) FOAMING EMULSIONS AND FOAMING COMPOSITIONS CONTAINING A POLYMER COMPRISING WATER-SOLUBLE UNITS AND UNITS WITH AN LCST, ESPECIALLY FOR COSMETIC USES

(75) Inventor: Florence L'Alloret, Paris (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/069,983

(22) PCT Filed: Jan. 11, 2002

(86) PCT No.: PCT/FR02/00100

§ 371 (c)(1),
(2), (4) Date: Mar. 14, 2002

(87) PCT Pub. No.: WO02/055606

PCT Pub. Date: Jul. 18, 2002

(65) Prior Publication Data

US 2003/0158330 A1 Aug. 21, 2003

(30) Foreign Application Priority Data

Jan. 15, 2001 (FR) .................................. 01 00480

(51) Int. Cl.
*A61K 8/91* (2006.01)
*A61K 8/90* (2006.01)
*A61K 8/04* (2006.01)
*A61K 8/81* (2006.01)
*A61K 8/84* (2006.01)
*A61Q 1/00* (2006.01)

(52) U.S. Cl. .............. 514/772.1; 514/772.2; 514/772.3; 514/772.4

(58) Field of Classification Search .................. 524/801, 524/800, 804; 514/772.1, 772.2, 772.3, 772.4
See application file for complete search history.

(56) References Cited

U.S. PATENT DOCUMENTS

| | | | | |
|---|---|---|---|---|
| 4,274,977 A | * | 6/1981 | Koerner et al. | ............... 516/117 |
| 4,559,226 A | * | 12/1985 | Fogel et al. | ................... 424/66 |
| 4,737,265 A | * | 4/1988 | Merchant et al. | ............ 208/188 |
| 4,839,167 A | * | 6/1989 | Yamamoto et al. | ....... 424/70.12 |
| 5,338,352 A | * | 8/1994 | Breneman et al. | ............ 106/285 |
| 5,550,225 A | | 8/1996 | Philippe | |
| 5,939,485 A | | 8/1999 | Bromberg et al. | |
| 6,159,457 A | | 12/2000 | Mougin | |
| 2002/0187173 A1 | | 12/2002 | L'Alloret et al. | |

FOREIGN PATENT DOCUMENTS

| | | |
|---|---|---|
| EP | 0 583 814 | 2/1994 |
| EP | 583814 A1 * | 2/1994 |
| EP | 0 629 649 | 12/1994 |
| EP | 629649 A1 * | 12/1994 |
| EP | 1055694 A2 * | 11/2000 |
| JP | S60-251924 | 12/1985 |
| JP | 61245835 | * 11/1986 |
| JP | 07-222919 | 8/1995 |
| JP | 09-067244 | 3/1997 |
| JP | 09-227329 | 9/1997 |
| JP | 2004-620339 | 7/2004 |
| WO | 95 24430 | 9/1995 |
| WO | 97 00275 | 1/1997 |
| WO | 97/12597 | 4/1997 |
| WO | 98 29487 | 7/1998 |
| WO | 98/48768 | 11/1998 |
| WO | 99 27924 | 6/1999 |
| WO | 00/35961 | 6/2000 |
| WO | 02055051 | 7/2002 |

OTHER PUBLICATIONS

A. Durand et al.: "Synthesis and thermoassociative properties in aqueous solution of graft copolymers containing poly(N-isopropylacrylamide) side chains" POLYMER, vol. 40, No. 17, pp. 4941-4951 Aug. 1999.
D. Hourdet et al.: "Reversible thermothickening of aqueous polymer solutions" POLYMER, vol. 35, No. 12, pp. 2624-2630 1994.
F. L'Alloret et al.: "Aqueous solution behavior of new thermoassociative polymers" Colloid & Polymer Science, vol. 273, No. 12, pp. 1163-1173 1995.
F. L'Alloret et al.: "Reversible thermoassociation of water-soluble polymers" Revue De L'Institute Francaise Du Petrole, vol. 52, No. 2, pp. 117-128 1997.

* cited by examiner

*Primary Examiner*—Kelechi C Egwim
(74) *Attorney, Agent, or Firm*—Oblon, Spivak, McClelland, Maier & Neustadt, L.L.P.

(57) ABSTRACT

A method of lowering the surface tension or the interface tension of water in cosmetic compositions comprising at least one cosmetic or dermatological adjuvant, the method comprising adding a polymer comprising water-soluble units and units with an LCST, wherein the LCST units an have in water a demixing temperature of from 5 to 40° C. for a concentration of 1% by mass is used, the polymer being present in a concentration such that the gel point of the aqueous phase is from 5 to 40° C., to ensure the stability of the dispersions at temperatures from 4° C. to 50° C.

14 Claims, No Drawings

FOAMING EMULSIONS AND FOAMING COMPOSITIONS CONTAINING A POLYMER COMPRISING WATER-SOLUBLE UNITS AND UNITS WITH AN LCST, ESPECIALLY FOR COSMETIC USES

TECHNICAL FIELD

The present invention relates to a novel use of polymers comprising water-soluble units and units with an LCST, in particular in foaming emulsions and compositions, that are especially cosmetic.

PRIOR ART

Polymers comprising water-soluble units and units with an LCST have been described in the following documents: D. Hourdet et al., Polymer, 1994, Vol. 35, No. 12, pages 2624 to 2630 [1]; F. L'Alloret et al., Coll. Polym. Sci., 1995, Vol. 273, No. 12, pages 1163-1173 [2]; F. L'Alloret et al., Revue de l'Institut Francais du Pétrole, 1997, Vol. 52, No. 2, pages 117-128 [3]; EP-A-0 583 814 [41] and EP-A-0 629 649 [5].

As described in these documents, these polymers comprise water-soluble units and units with an LCST, which have in water a lower critical solution temperature. Thus, these units with an LCST are units whose solubility in water is modified beyond a certain temperature. They are units having a heat-induced demixing temperature (or cloud point) defining their region of water solubility. The minimum demixing temperature obtained as a function of the polymer concentration is known as the "LCST" (Lower Critical Solution Temperature). For each polymer concentration, a heat-induced demixing temperature is observed; it is higher than the LCST, which is the minimum point of the curve. Below this temperature, the polymer is water-soluble, and above this temperature, the polymer loses its water solubility.

Thus, these polymers have water-gelling properties brought about by increasing the temperature. These properties may be exploited for uses in the petroleum field, as described in documents [4] and [5].

WO-A-95/24430 [6] also describes copolymers comprising units with an LCST and pH-sensitive units, which have heat-induced gelling properties. These copolymers are used for the controlled release of active principles in the pharmaceutical field and in the cosmetic field, in the form of solid particles or in formulations such as liquids, gels or ointments. The gels obtained with these copolymers are opaque and have an LCST, unlike the polymers of the invention which comprise units with an LCST but whose overall behaviour is not of LCST type and which lead to transparent gels.

U.S. Pat. No. 5,939,485 [7] and WO 97/00275 [8] describe reversible-gelling polymer systems comprising a sensitive component capable of aggregating in response to a change in an external stimulus and a structural component. The external stimulus may be the temperature. The sensitive component may be a block copolymer such as a Poloxamer, for example a Pluronic®, which aggregates microscopically beyond a critical temperature not corresponding to an LCST. A non-ionic surfactant may also be used as a sensitive component. These polymers have heat-induced gelling properties and may be used in the pharmaceutical field to deliver medicinal products and in many other fields including the cosmetics field. Example 34 of WO 97/00275 [8] illustrates cosmetic formulations comprising the poloxamer-acrylic derivative system with addition of nonionic, anionic and cationic surfactants.

In these formulations, the sensitive component of the polymer system has a different behaviour from that of units with an LCST during heating. Thus, when it is heated to about 30-40° C., it exhibits a temperature of micellization, that is to say an aggregation at the microscopic scale, and then, when it is heated further, a higher LCST temperature. This LCST corresponds to a macroscopic aggregation between the molecules. It is explained in WO-A-97/00275 [8] on pages 16 and 17 that the gelation and the LCST are observed at temperatures that differ by about 70° C. This shows that these polymers are different from those of our application.

Document WO-A-98/48768 [9] also discloses cosmetic compositions using a reversible heat-induced gelling polymer system, comprising polyacrylic acid and a poloxamer. This polymer is thus different from the polymers of the invention.

WO-A-00/35961 [10] describes the preparation of polymers with properties of heat-induced thickening by emulsion polymerization and the use of these polymers in pharmaceutical and cosmetic compositions. These polymers may be copolymers containing water-soluble units and units with an LCST based on alkylene oxide. It is envisaged to add non-ionic surfactants to the polymers to reinforce their heat-induced thickening properties.

Thus, it emerges from these documents that polymers comprising water-soluble units and units with an LCST have heat-induced gelling or heat-induced thickening properties.

DESCRIPTION OF THE INVENTION

According to the invention, it has been discovered that polymers comprising water-soluble units and units with an LCST, the units with an LCST having in water a demixing temperature of from 5 to 40° C. at a concentration of 1% by mass in water, furthermore had the advantageous property of lowering the surface tension or the interface tension of the water, and of consequently being able to be used for the manufacture of foaming compositions and emulsions.

Thus, one subject of the invention is the use of a polymer comprising water-soluble units and units with an LCST, the units with an LCST having in water a demixing temperature of from 5 to 40° C. at a concentration of 1% by mass in water, to lower the surface tension or the interface tension of water.

According to one advantageous characteristic of the invention, the lowering of the surface tension or of the interface tension of water is of at least 15 mN/m for a concentration of polymer in water of 0.1% by mass in the temperature range from 5 to 80° C.

Moreover, this effect of lowering the surface tension or the interface tension of water is reinforced when the temperature becomes higher than the demixing temperature of the units with an LCST. In this case, the lowering of the surface tension or of the interface tension of water is of at least 20 mN/m for a concentration of polymer in water of 0.1% by mass when the temperature is higher than the demixing temperature of the units with an LCST at this concentration.

These interface properties of polymers comprising water-soluble units and units with an LCST may be exploited for the manufacture of foams, oil-in-water emulsions or water-in-oil-in-water (W/O/W) multiple emulsions, without surfactant or containing a very small amount of surfactant.

Foams are dispersions of bubbles of gas, in particular of air, in an aqueous continuous phase. In cosmetic cleansing compositions, these bubbles are stabilized by surfactants whose concentration ranges from 5% to 20% by mass. These amphiphilic species of low molecular mass (M<2000 g/mol) have the drawback of having a relatively aggressive nature with respect to the skin.

Oil-in-water (O/W) emulsions are dispersions of oily globules in an aqueous continuous phase. These cosmetic O/W emulsions or W/O/W multiple emulsions may be stabilized by amphiphilic species of varied nature:
- surfactants, which are characterized by their low molar mass (<2000 g/mol),
- amphiphilic gelling agents of microgel type, such as Pemulen TR1 (Goodrich), and
- dimethicone copolyol derivatives used in the presence of silicone oil.

Each of these compounds has limitations for use:
- surfactants have a relatively aggressive nature with respect to the skin;
- amphiphilic gelling agents of microgel type are limited in number and all lead to gelled textures of the same type,
- dimethicone copolyol derivatives are specific for silicone oils.

Moreover, the stability of the emulsions is generally reduced when the temperature increases, which may lead to phenomena of phase separation during storage of the emulsions on account of variations in temperature.

Thus, for cosmetic uses, it is advantageous to have available agents:
- that allow cosmetic emulsions and foams to be stabilized, especially over a wide temperature range (5° C.-80° C.),
- that have little aggressive nature on the skin, and
- that can give a wide range of textures, fluid or thickened/gelled.

According to the invention, it has been found that polymers comprising water-soluble units and units with an LCST with suitable demixing temperatures make it possible to obtain foams and emulsions without surfactant or containing only a very small amount of surfactant, and thus having little aggressive nature on the skin, that are stable in the temperature range from 5 to 80° C. and that can give a wide range of textures.

Thus, a subject of the invention is also a foaming composition comprising an aqueous phase containing a polymer comprising water-soluble units and units with an LCST, the units with an LCST having in water a demixing temperature of from 5 to 40° C. at a concentration of 1% by mass in water.

The invention also relates to an oil-in-water emulsion comprising an aqueous phase and an oily phase dispersed in the aqueous phase, in which the aqueous phase comprises a polymer comprising water-soluble units and units with an LCST, the units with an LCST having in water a demixing temperature of from 5 to 40° C. at a concentration of 1% by mass in water.

The invention also relates to a water-in-oil-in-water emulsion comprising a water-in-oil emulsion dispersed in an outer aqueous phase, in which the outer aqueous phase comprises a polymer comprising water-soluble units and units with an LCST, the units with an LCST having in water a demixing temperature of from 5 to 40° C. at a concentration of 1% by mass in water.

The polymers used in the invention may be block polymers or grafted polymers, which comprise, on the one hand, water-soluble units and, on the other hand, units with an LCST as defined above.

The polymers used in the context of the invention may thus be block polymers comprising, for example, water-soluble blocks alternating with LCST blocks.

These polymers may also be in the form of grafted polymers whose backbone is formed from water-soluble units, bearing LCST grafts. These polymers may also be in the form of grafted polymers whose backbone is formed from units with an LCST, bearing water-soluble grafts.

These structures may be partially crosslinked.

It is pointed out in the present text that the terms "water-soluble unit" and "LCST unit" do not include the groups linking together, on the one hand, the water-soluble units and, on the other hand, the units with an LCST, the linking units being derived from the reaction of the reactive sites borne, on the one hand, by precursors of the water-soluble units and, on the other hand, by precursors of the units with an LCST.

Water-soluble units in these polymers are units that are soluble in water at a temperature of from 5° C. to 80° C., to a proportion of at least 10 g/l and preferably at least 20 g/l.

However, the term "water-soluble units" also means units not necessarily having the solubility mentioned above, but which in aqueous solution at 1% by weight, from 5° C. to 80° C., allow the production of a solution that is macroscopically homogeneous and transparent, that is to say having a maximum light transmittance value, irrespective of the wavelength of between 400 and 800 nm, through a sample 1 cm thick, of at least 85% and preferably of at least 90%.

These water-soluble units do not have a heat-induced demixing temperature of LCST type.

These water-soluble units may be obtained by free-radical polymerization of vinyl monomers, or by polycondensation, or alternatively may consist of natural polymers or modified existing natural polymers.

By way of example, mention may be made of the following monomers, which may be used to form the said water-soluble units, alone or as a mixture:
- (meth)acrylic acid;
- vinyl monomers of formula (I) below:

in which:
R is chosen from H, —CH$_3$, —C$_2$H$_5$ or —C$_3$H$_7$, and
X is chosen from:
- alkyl oxides of —OR' type in which R' is a linear or branched, saturated or unsaturated hydrocarbon radical containing from 1 to 6 carbon atoms, optionally substituted with at least one halogen atom (iodine, bromine, chlorine or fluorine); a sulphonic (—SO$_3^-$), sulphate (—SO$_4^-$), phosphate (—PO$_4$H$_2$); hydroxyl (—OH); primary amine (—NH$_2$); secondary amine (—NHR$_1$), tertiary amine (—NR$_1$R$_2$) or quaternary amine (-N$^+$R$_1$R$_2$R$_3$) group with R$_1$, R$_2$ and R$_3$ being, independently of each other, a linear or branched, saturated or unsaturated hydrocarbon radical containing 1 to 6 carbon atoms, with the proviso that the sum of the carbon atoms of R'+R$_1$+R$_2$+R$_3$ does not exceed 7; and
- —NH$_2$, —NHR$_4$ and —NR$_4$R$_5$ groups in which R$_4$ and R$_5$ are, independently of each other, linear or branched, saturated or unsaturated hydrocarbon radicals containing 1 to 6 carbon atoms, with the proviso that the total number of carbon atoms in R$_4$+R$_5$ does not exceed 7, the said R$_4$ and R$_5$ optionally being substituted with a halogen atom (iodine, bromine, chlorine or fluorine) ; a hydroxyl (—OH); sulphonic (—SO$_3^-$), sulphate (—SO$_4^-$); phosphate (—PO$_4$H$_2$);

primary amine (—NH₂); secondary amine (—NHR₁), tertiary amine (—NR₁R₂) and/or quaternary amine (N⁺R₁R₂R₃) group with R₁, R₂ and R₃ being, independently of each other, a linear or branched, saturated or unsaturated hydrocarbon radical containing 1 to 6 carbon atoms, with the proviso that the sum of the carbon atoms of R₄+R₅+R₁+R₂+R₃ does not exceed 7;

maleic anhydride;

itaconic acid;

vinyl alcohol of formula CH₂=CHOH;

vinyl acetate of formula CH₂=CH—OCOCH₃;

N-vinyllactams such as N-vinylpyrrolidone, N-vinylcaprolactam and N-butyrolactam;

vinyl ethers of formula CH₂=CHOR₆ in which R₆ is a linear or branched, saturated or unsaturated hydrocarbon radical containing from 1 to 6 carbons;

water-soluble styrene derivatives, especially styrene sulphonate;

dimethyldiallylammonium chloride; and vinylacetamide.

Among the polycondensates and the natural polymers or modified natural polymers that may constitute all or part of the water-soluble units, mention may be made of:

water-soluble polyurethanes, xanthan gum, especially the product sold under the names Keltrol T and Keltrol SF by Kelco; or Rhodigel SM and Rhodigel 200 from Rhodia;

alginates (Kelcosol from Monsanto) and derivatives thereof such as propylene glycol alginate (Kelcoloid LVF from Kelco);

cellulose derivatives and especially carboxymethylcellulose (Aquasorb A500, Hercules), hydroxypropylcellulose, hydroxy-ethylcellulose and quaternized hydroxyethylcellulose;

galactomannans and derivatives thereof, such as Konjac gum, guar gum, hydroxypropylguar, hydroxypropylguar modified with sodium methylcarboxylate groups (Jaguar XC97-1, Rhodia), hydroxypropyltrimethylammonium guar chloride.

Mention may also be made of polyethyleneimine.

The water-soluble units preferably have a molar mass ranging from 1000 g/mol to 5 000 000 g/mol when they constitute the water-soluble backbone of a grafted polymer.

These water-soluble units preferably have a molar mass ranging from 500 g/mol to 100 000 g/mol when they constitute one block of a multiblock polymer or alternatively when they constitute the grafts of a grafted polymer or comb polymer.

The units with an LCST of the polymers used in the invention may be defined as being units whose water solubility is modified beyond a certain temperature. They are units with a heat-induced demixing temperature (or cloud point) defining their region of solubility in water. The minimum demixing temperature obtained as a function of the polymer concentration is referred to as the "LCST" (Lower Critical Solution Temperature). For each polymer concentration, a heat-induced demixing temperature is observed; it is higher than the LCST, which is the minimum point of the curve. Below this temperature, the polymer is soluble in water; above this temperature, the polymer loses its solubility in water.

The expression "soluble in water at a temperature T" means that the units have a solubility at T of at least 1 g/l and preferably of at least 2 g/l.

The measurement of the LCST may be performed visually: the temperature at which the cloud point of the aqueous solution appears is determined; this cloud point is reflected by the opacification of the solution, or the loss of transparency.

In general, a transparent composition will have a maximum light transmittance value, irrespective of the wavelength of between 400 and 800 mm, through a sample 1 cm thick, of at least 85% and preferably of at least 90%.

The transmittance may be measured by placing a sample 1 cm thick in the light beam of a spectrophotometer working at the wavelengths of the light spectrum.

The units with an LCST in the polymers used in the invention may consist of one or more of the following polymers:

polyethers such as polyethylene oxide (PEO), polypropylene oxide (PPO) or random copolymers of ethylene oxide (EO) and of propylene oxide (PO), polyvinyl methyl ether, poly-N-isopropylacrylamide and poly-N-ethylacrylamide, and polyvinylcaprolactam.

Preferably, the units with an LCST consist of polypropylene oxide (PPO)ₙ with n being an integer from 10 to 50, or random copolymers of ethylene oxide (EO) and of propylene oxide (PO), represented by the formula:

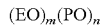

in which m is an integer ranging from 1 to 40 and preferably from 2 to 20, and n is an integer ranging from 10 to 60 and preferably from 20 to 50.

Preferably, the molar mass of these units with an LCST is from 500 to 5300 g/mol and especially from 1500 to 4000 g/mol.

It has been found that the random distribution of the EO and PO units is reflected by the existence of a lower critical solution temperature, beyond which a macroscopic phase separation is observed. This behaviour is different from that of block (EO)(PO) copolymers, which form micelles beyond a critical temperature known as the micellization temperature (macroscopic aggregation).

The units with an LCST may thus especially be derived from aminated, especially monoamino, diamino or triamino, random copolymers of ethylene oxide and of propylene oxide. Among the commercially available units with an LCST that may be mentioned are the copolymers sold under the name Jeffamine by Huntsman, and especially Jeffamine XTJ-507 (M-2005), Jeffamine D-2000 and Jeffamine XTJ-509 (or T-3000).

The units with an LCST may also be derived from random EO/PO copolymers containing OH end groups, such as those sold under the name Polyglycols P41 and B11 by Clariant.

Polymeric and copolymeric N-substituted acrylamide derivatives having an LCST, and also polyvinylcaprolactam and vinyl caprolactam copolymers may also be used in the invention as units with an LCST.

As examples of polymeric N-substituted acrylamide derivatives having an LCST, mention may be made of poly-N-isopropylacrylamide, poly-N-ethylacrylamide and copolymers of N-isopropylacrylamide (or of N-ethylacrylamide) and of a vinyl monomer having the formula (I) given above, or of a monomer chosen from maleic anhydride, itaconic acid, vinylpyrrolidone, styrene and its derivatives, dimethyldiallylammonium chloride, vinylacetamide, vinyl ethers and vinyl acetate derivatives.

The molar mass of these polymers is preferably from 1000 g/mol to 500 000 g/mol and preferably from 2000 to 50 000 g/mol.

These polymers may be synthesized by free-radical polymerization using a pair of initiators such as aminoethanethiol hydrochloride, in the presence of potassium persulphate, so as to obtain units with an LCST with a reactive amino end group.

As examples of vinylcaprolactam copolymers, mention may be made of copolymers of vinylcaprolactam and of a vinyl monomer of formula (I) given above, or of a monomer chosen from maleic anhydride, itaconic acid, vinylpyrrolidone, styrene and its derivatives, dimethyldiallylammonium chloride, vinylacetamide, vinyl alcohol, vinyl acetate, vinyl ethers and vinyl acetate derivatives.

The molar mass of these vinylcaprolactam polymers or copolymers is generally from 1000 g/mol to 500 000 g/mol and preferably from 2000 to 50 000 g/mol.

These compounds may be synthesized by free-radical polymerization using a pair of initiators such as aminoethanethiol hydrochloride, in the presence of potassium persulphate, so as to obtain units with an LCST with a reactive amino end group.

The proportion by mass of units with an LCST in the final polymer is preferably from 5% to 70%, especially from 20% to 65% and particularly from 30% to 60% by weight relative to the final polymer.

As defined above, the demixing temperature of the said units with an LCST is from 5° C. to 40° C. and preferably from 10° C. to 35° C., for a concentration by mass in water of 1% by weight of the said units with an LCST.

The polymers used in the context of the invention may be readily prepared by a person skilled in the art on the basis of his general knowledge, using grafting, copolymerization or coupling reaction processes.

When the final polymer is in the form of a grafted polymer, especially having a water-soluble backbone with side chains with an LCST, it is possible to prepare it by grafting units with an LCST containing at least one reactive end group, especially an amino end group, onto a water-soluble polymer forming the backbone, bearing at least 10% (on a molar basis) of reactive groups such as carboxylic acid functions. This reaction may be carried out in the presence of a carbodiimide such as dicyclohexylcarbodiimide or 1-(3-dimethylaminopropyl)-3-ethylcarbodiimide hydrochloride, in a solvent such as N-methylpyrrolidone or water.

Another possibility for preparing grafted polymers consists in copolymerizing, for example, a macromonomer with an LCST (chain with an LCST described above with a vinyl end group) and a water-soluble vinyl monomer such as acrylic acid or vinyl monomers of formula (I).

When the final polymer is in the form of a block polymer, it is possible to prepare it by coupling between water-soluble units and units with an LCST, these units having complementary reactive sites at each end.

In the case of grafting processes and coupling processes, the reactive sites of the units with an LCST may be amine functions, especially monoamines, diamines or triamines, and OH functions. In this case, the reactive sites of the water-soluble units may be carboxylic acid functions.

As has been seen previously, the foaming compositions of the invention comprise an aqueous phase containing a polymer comprising water-soluble units and units with an LCST, as defined above. Generally, the concentration by mass of polymer in the aqueous phase is less than or equal to 5%, preferably from 0.01 to 5% and better still from 0.02 to 4% of the weight of the aqueous phase.

The aqueous phase may furthermore comprise a foaming surfactant in a small amount, for example in a concentration by mass of less than or equal to 5% and preferably less than or equal to 4% by weight relative to the weight of aqueous phase.

The foaming surfactants used may be nonionic, anionic, amphoteric or zwitterionic surfactants. Preferably, the foaming surfactant(s) is(are) chosen from nonionic surfactants.

Nonionic surfactants that may be mentioned, for example, are alkylpolyglycosides (APG), esters of polyols and of fatty acids, esters of polyethylene glycols and of fatty acids, derivatives of fatty alcohols and of polyols (ethers), and oxyalkylenated (oxyethylenated and/or oxypropylenated) derivatives of these compounds. Mention may also be made of maltose esters, polyglycerolated fatty alcohols, glucamine derivatives, for instance 2-ethylhexyloxycarbonyl-N-methylglucamine, and mixtures thereof.

Alkylpolyglucosides which may be mentioned, for example, are decylglucoside (Alkyl-C9/C11-polyglucoside (1.4)), for instance the product solid under the name Mydol 10 by the company Kao Chemicals, the product sold under the name Plantaren 2000 UP and Plantacare 2000 UP by the company Henkel, and the product sold under the name Oramix NS 10 by the company SEPPIC; caprylyl/capryl glucoside, for instance the product sold under the name Oramix CG 110 by the company SEPPIC or under the name Lutensol GD 70 by the company BASF; laurylglucoside, for instance the products sold under the names Plantaren 1200 N and Plantacare 1200 by the company Henkel; and coco-glucoside, for instance the product sold under the name Plantacare 818/UP by the company Henkel, and mixtures thereof.

The maltose derivatives are, for example, those described in document EP-A-566 438 [11], such as O-octanoyl-6'-D-maltose or O-dodecanoyl-6'-D-maltose described in document FR-2 739 566 [12].

Among the polyglycerolated fatty alcohols that may be mentioned are polyglycerolated dodecanediol (3.5 mol of glycerol), this product being sold under the name Chimexane NF by the company Chimex. Anionic surfactants which may be used, for example, are carboxylates, amino acid derivatives, alkyl sulphates, alkyl ether sulphates, sulphonates, isethionates, taurates, sulphosuccinates, alkyl sulphoacetates, phosphates and alkyl phosphates, polypeptides, anionic derivatives of alkyl polyglucoside, fatty acid soaps, and mixtures thereof.

Carboxylates which may be mentioned, for example, are alkali metal salts of N-acylamino acids; amidoether carboxylates (AEC), for instance sodium lauryl amidoether carboxylate (3 EO) sold under the name Akypo Foam 30 by the company Kao Chemicals; polyoxyethylenated carboxylic acid salts, for instance oxyethylenated (6 EO) sodium lauryl ether carboxylate (65/25/10 C12-14-16) sold under the name Akypo Soft 45 NV by the company Kao Chemicals; polyoxyethylenated fatty acids of olive oil and of carboxymethyl, for instance the product sold under the name Olivem 400 by the company Biologia E Tecnologia; oxyethylenated (6 EO) sodium tridecyl ether carboxylate sold under the name Nikkol ECTD-6NEX by the company Nikkol; sodium 2-(2-hydroxyalkyloxy) acetate sold under the name Beaulight SHAA by the company Sanyo.

The amino acid derivatives may be chosen, for example, from sarcosinates and especially acyl sarcosinates, for instance sodium lauroyl sarcosinate sold under the name Sarkosyl NL 97 by the company Ciba or sold under the name Oramix L 30 by the company SEPPIC, sodium myristoyl sarcosinate, sold under the name Nikkol Sarcosinate MN by the company Nikkol, sodium palmitoyl sarcosinate, sold under the name Nikkol Sarcosinate PN by the company Nikkol; alaninates, for instance sodium lauroyl-N-methylamidopropionate sold under the name Sodium Nikkol Alaninate LN 30 by the company Nikkol or sold under the name Alanone Ale by the company Kawaken, and triethanolamine N-lauroyl-N-methylalanine, sold under the name Alanone Alta by the company Kawaken; N-acylglutamates, for instance triethanolamine monococoylglutamate sold under the name Acylglutamate CT-12 by the company Ajinomoto, triethanolamine lauroyl glutamate sold under the name Acylglutamate LT-12 by the company Ajinomoto and monosodium N-lauroyl-L-glutamate sold under the name Amisoft LS-11 by the company Ajinomoto; aspartates, for instance the mixture of triethanolamine N-lauroylaspartate and triethanolamine N-myristoylaspartate, sold under the name Asparack LM-TS2 by the company Mitsubishi; citrates, and mixtures thereof.

Glycine derivatives that may be mentioned are sodium N-cocoylglycinate and potassium N-cocoylglycinate, for instance the products sold under the names Amilite GCS-12 and Amilite GCK-12 by the company Ajinomoto.

Alkyl ether sulphates that may be mentioned, for example, are sodium lauryl ether sulphate (70/30 C12-14) (2.2 EO) sold under the names Sipon AOS 225 or Texapon N702 Pate by the company Henkel, ammonium lauryl ether sulphate (70/30 C12-14) (3 EO) sold under the name Sipon LEA 370 by the company Henkel, and ammonium (C12-C14)alkyl ether (9 EO) sulphate sold under the name Rhodapex AB/20 by the company Rhodia Chimie.

Sulphonates that may be mentioned, for example, are α-olefin sulphonates, for instance sodium α-olefin sulphonate (C14-16) sold under the name Bio-Terge AS-40 by the company Stepan, sold under the names Witconate AOS Protege and Sulframine AOS PH 12 by the company Witco or sold under the name Bio-Terge AS-40 CG by the company Stepan, secondary sodium olefin sulphonate sold under the name Hostapur SAS 30 by the company Clariant; linear alkyl aryl sulphonates, for instance sodium xylene sulphonate sold under the names Manrosol SXS30, Manrosol SXS40 and Manrosol SXS93 by the company Manro.

Isethionates that may be mentioned are acylisethionates, for instance sodium cocoyl isethionate, such as the product sold under the name Jordapon CI P by the company Jordan.

Taurates that may be mentioned are the sodium salt of palm kernel oil methyl taurate sold under the name Hostapon CT Pâte by the company Clariant; N-acyl N-methyltaurates, for instance sodium N-cocoyl N-methyltaurate sold under the name Hostapon LT-SF by the company Clariant or sold under the name Nikkol CMT-30-T by the company Nikkol, and sodium palmitoyl methyltaurate sold under the name Nikkol PMT by the company Nikkol.

Sulphosuccinates that may be mentioned, for example, are oxyethylenated (3 EO) lauryl mono-sulphosuccinate (70/30 C12-C14) sold under the names Setacin 103 Special, Rewopol SB-FA 30 K 4 by the company Witco, the disodium salt of a C12-C14 alkyl hemisulphosuccinate, sold under the name Setacin F Special Paste by the company Zschimmer Schwarz, oxyethylenated (2 EO) disodium oleamidosulphosuccinate sold under the name Standapol SH 135 by the company Henkel, oxyethylenated (5 EO) lauramide monosulphosuccinate sold under the name Lebon A-5000 by the company Sanyo, the disodium salt of oxyethylenated (10 EO) lauryl citrate monosulphosuccinate sold under the name Rewopol SB CS 50 by the company Witco, and ricinoleic monoethanolamide monosulphosuccinate sold under the name Rewoderm S 1333 by the company Witco.

Phosphates and alkyl phosphates that may be mentioned, for example, are monoalkyl phosphates and dialkyl phosphates, such as lauryl monophosphate sold under the name MAP 20 by the company Kao Chemicals, the potassium salt of dodecylphosphoric acid, as a mixture of monoester and diester (predominantly diester) sold under the name Crafol AP-31 by the company Cognis, the mixture of monoester and diester of octylphosphoric acid, sold under the name Crafol AP-20 by the company Cognis, the mixture of ethoxylated (7 mol of EO) 2-butyloctanol monoester and diester of phosphoric acid, sold under the name Isofol 12 7 EO-Phosphate Ester by the company Condea, the potassium or triethanolamine salt of mono(C12-C13) alkyl phosphate sold under the references Arlatone MAP 230K-40 and Arlatone MAP 230T-60 by the company Uniqema, and potassium lauryl phosphate sold under the name Dermalcare MAP XC-99/09 by the company Rhodia Chimie.

The polypeptides are obtained, by condensing a fatty chain onto the amino acids of cereals and especially of wheat and oat. Polypeptides that may be mentioned, for example, are the potassium salt of hydrolyzed lauroyl wheat protein, sold under the name Aminofoam W OR by the company Croda, the triethanolamine salt of hydrolyzed cocoyl soybean protein, sold under the name May-Tein SY by the company Maybrook, the sodium salt of oat lauroyl amino acids, sold under the name Proteol Oat by the company SEPPIC, collagen hydrolyzate grafted onto coconut fatty acid, sold under the name Geliderm 3000 by the company Deutsche Gelatine, soybean proteins acylated with hydrogenated coconut acids, sold under the name Proteol VS 22 by the company SEPPIC.

The anionic alkyl-polyglucoside derivatives may especially be citrates, tartrates, sulphosuccinates, carbonates and glycerol ethers obtained from alkyl polyglucosides. Examples that may be mentioned are the sodium salt of cocoylpolyglucoside tartaric ester (1,4), sold under the name Eucarol AGE-ET by the company Cesalpinia, the disodium salt of cocoylpolyglucoside sulphosuccinic ester (1,4), sold under the name Essai 512 MP by the company SEPPIC, the sodium salt of cocoyl polyglucoside citric ester (1,4) sold under the name Eucarol AGE-EC® by the company Cesalpinia. Another anionic holoside derivative may be sodium dodecyl-D-galactoside uronate sold under the name Dodecyl-D-Galactoside Uronate de Sodium by the company Soliance.

Fatty acid soaps that may be used as anionic surfactants are fatty acids of natural or synthetic origin, salified with a mineral or organic base. The fatty chain may contain from 6 to 22 carbon atoms and preferably from 8 to 18 carbon atoms. The mineral or organic base may be chosen from alkali metals and alkaline-earth metals, amino acids and amino alcohols. Salts that may be used, for example, are the sodium, potassium, magnesium, triethanolamine, N-methylglucamine, lysine and arginine salts. Soaps that may be mentioned, for example, are the potassium or sodium salts of lauric, myristic, palmitic or stearic acid (potassium or sodium laurate, myristate, palmitate or stearate), and mixtures thereof.

Amphoteric and zwitterionic surfactants that may be used, for example, are betaines, N-alkylamidobetaines and derivatives thereof, glycine derivatives, sultaines, alkyl polyaminocarboxylates and alkylamphoacetates, and mixtures thereof.

Betaines that may be mentioned, for example, are cocobetaine, for instance the product sold under the name Dehyton AB-30 by the company Henkel, laurylbetaine, for instance the product sold under the name Genagen KB by the company Clariant, oxyethylenated (10 EO) laurylbetaine, for instance the product sold under the name Lauryl Ether (10 EO) Betaine by the company Shin Nihon Rica, oxyethylenated stearylbetaine (10 EO), for instance the product sold under the name Stearyl Ether (10 EO) Betaine by the company Shin Nihon Rica. Examples of N-alkylamido betaines and derivatives thereof that may be mentioned are cocoamidopropyl betaine sold under the name Lebon 2000 HG by the company Sanyo, or sold under the name Empigen BB by the company Albright & Wilson, and lauramidopropyl betaine sold under the name Rewoteric AMB12P by the company Witco.

Examples of sultaines that may be mentioned include cocoylamidopropylhydroxysulphobetaine sold under the name Crosultaine C-50 by the company Croda.

Examples of alkyl polyaminocarboxylates (APAC) that may be mentioned are sodium cocoylpolyaminocarboxylate, sold under the name Ampholak 7 CX/C and Ampholak 7 CX by the company Akzo Nobel, sodium stearylpolyamidocarboxylate, sold under the name Ampholak 7 TX/C by the company Akzo Nobel, and sodium carboxymethyloleylpolypropylamine sold under the name Ampholak XO7/C by the company Akzo Nobel.

Examples of alkylamphoacetates that may be mentioned are N-disodium N-cocoyl-N-carboxymethoxyethyl-N-carboxymethylethylenediamine (CTFA name: disodium cocamphodiacetate), for instance the product sold under the name Miranol C2M Concentré NP by the company Rhodia Chimie, and N-sodium N-cocoyl-N-hydroxyethyl-N-carboxymethylethylenediamine (CTFA name: sodium cocamphoacetate).

Among these surfactants, those that may be in powder form are, for example, sodium cocoylisethionate, ricinoleic monoethanolamide monosulphosuccinate sold under the name Rewoderm S 1333 by the company Witco, monosodium N-lauroyl-L-glutamate (Amisoft LS-11) and sodium palmitoyl methyltaurate sold under the name Nikkol PMT by the company Nikkol.

In the case of the oil-in-water emulsions of the invention, the aqueous phase comprises a polymer comprising water-soluble units and units with an LCST, as defined above, and the concentration by mass of polymer in the aqueous phase is less than or equal to 5%, preferably from 0.01 to 5% and better still from 0.02 to 4% by weight of aqueous phase.

The aqueous phase may furthermore contain an additional emulsifying surfactant in very small amounts, not exceeding 1%.

Emulsifying surfactants that may especially be mentioned are nonionic emulsifiers and, for example, the products of addition of from 1 to 200 mol of ethylene oxide or of propylene oxide to partial esters of polyols containing 2 to 16 carbon atoms and of fatty acids containing 12 to 22 carbon atoms, for instance fatty acid esters of polyethylene glycol such as PEG-100 stearate, PEG-50 stearate and PEG-40 stearate; fatty acid esters of polyols such as glyceryl stearate, sorbitan tristearate and oxyethylenated sorbitan stearates sold under the trade names Tween® 20 or Tween® 60, sugar esters, for instance sucrose stearate, and mixtures thereof.

In the foaming compositions and the emulsions of the invention, the aqueous phase may consist of a physiologically acceptable medium allowing a topical application and especially a cosmetic application.

In the present patent application, the expression "physiologically acceptable medium" means a medium that is compatible with all keratin materials such as the skin, including the scalp, the nails, mucous membranes, the eyes and the hair or any other area of body skin.

The physiologically acceptable medium for the foaming compositions and the emulsions of the invention comprises water. The amount of water may range from 20 to 99.98% by weight and preferably from 40 to 95% by weight relative to the total weight of the composition.

The water used may be, besides water, a floral water such as cornflower water, a mineral water such as eau de Vittel, eau de Lucas or eau de la Roche Posay and/or a spring water.

The physiologically acceptable medium may contain, besides water, one or more solvents chosen from lower alcohols containing from 1 to 8 carbon atoms, such as ethanol; polyols such as glycerol; glycols, for instance butylene glycol, isoprene glycol, propylene glycol and polyethylene glycols such as PEG-8; sorbitol; sugars such as glucose, fructose, maltose, lactose and sucrose; and mixtures thereof. The amount of solvent(s) may range from 0.5 to 30% by weight and preferably from 5 to 20% by weight relative to the total weight of the composition.

The oily phase present in the emulsions and optionally present in the foaming compositions may consist of any fatty substance used in cosmetics.

The oily phase preferably comprises at least one oil.

As oils which can be used in the composition of the invention, mention may be made for example of:
  hydrocarbon-based oils of animal origin, such as perhydrosqualene;
  hydrocarbon-based plant-origin oils, such as liquid triglycerides of fatty acids of 4 to 10 carbon atoms, such as heptanoic or octanoic acid triglycerides or alternatively, for example, sunflower oil, corn oil, soybean oil, marrow oil, grapeseed oil, sesame oil, hazelnut oil, apricot oil, macadamia oil, arara oil, castor oil, avocado oil, caprylic/capric acid triglycerides such as those sold by the company Stearineries Dubois or those sold under the names Miglyol 810, 812 and 818 by the company Dynamit Nobel, jojoba oil or karite butter;
  synthetic esters and ethers in particular of fatty acids, such as the oils of formulae $R^1COOR^2$ and $R^1OR^2$ in which $R^1$ represents a fatty acid residue containing from 8 to 29 carbon atoms and $R^2$ represents a branched or unbranched hydrocarbon chain containing from 3 to 30 carbon atoms, such as, for example, purcellin oil, isononyl isononanoate, isopropyl myristate, 2-ethylhexyl palmitate, 2-octyldodecyl stearate, 2-octyldodecyl erucate or isostearyl isostearate; hydroxylated esters such as isostearyl lactate, octyl hydroxystearate, octyldodecyl hydroxystearate, diisostearyl malate, triisocetyl citrate, and fatty alcohol heptanoates, octanoates and decanoates; polyol esters such as propylene glycol dioctanoate, neopentyl glycol diheptanoate and diethylene glycol diisononanoate; and pentaerythritol esters such as pentaerythrityl tetraisostearate;
  linear or branched hydrocarbons of mineral or synthetic origin, such as volatile or non-volatile liquid paraffins and derivatives thereof, petroleum jelly, polydecenes or hydrogenated polyisobutene such as Parleam oil;
  natural or synthetic essential oils such as, for example, eucalyptus oil, hybrid lavender oil, lavender oil, vetiver oil, Litsea cubeba oil, lemon oil, sandalwood oil, rosemary oil, camomile oil, savory oil, nutmeg oil, cinnamon oil, hyssop oil, caraway oil, orange oil, geraniol oil, cade oil and bergamot oil;
  fatty alcohols containing from 8 to 26 carbon atoms, such as cetyl alcohol, stearyl alcohol, and the mixture thereof (cetylstearyl alcohol), octyldodecanol, 2-butyloctanol, 2-hexyldecanol, 2-undecylpentadecanol, oleyl alcohol or linoleyl alcohol;
  partially hydrocarbon-based and/or silicone-based fluoro oils such as those described in document JP-A-2-295 912;
  silicone oils such as volatile or non-volatile polydimethylsiloxanes (PDMSs) containing a linear or cyclic silicone chain, which are liquid or pasty at room temperature, in particular cyclo-polydimethylsiloxanes (cyclomethicones) such as cyclohexasiloxane; polydimethylsiloxanes comprising alkyl, alkoxy or phenyl groups, pendant or at the end of a silicone chain, these groups containing from 2 to 24 carbon atoms; phenylsilicones such as phenyl trimethicones, phenyl dimethicones, phenyltrimethylsiloxydiphenylsiloxanes, diphenyl dimethicones, diphenylmethyldiphenyltrisiloxanes, 2-phenylethyl trimethylsiloxysilicates and polymethylphenylsiloxanes;

mixtures thereof.

The term "hydrocarbon-based oil" in the list of abovementioned oils embraces any oil comprising predominantly carbon and hydrogen atoms, and optionally ester, ether, fluoro, carboxylic acid and/or alcohol groups.

The other fatty substances which may be present in the oily phase are, for example, fatty acids containing from 8 to 30 carbon atoms, for instance stearic acid, lauric acid, palmitic acid and oleic acid; waxes, for example lanolin, beeswax, carnauba wax, candelilla wax, paraffin wax, lignite wax or microcrystalline waxes, ceresine or ozokerite, synthetic waxes, for instance polyethylene waxes and Fischer-Tropsch waxes; gums such as silicone gums (dimethiconol); silicone resins such as trifluoromethyl-C1-4-alkyldimethicone and trifluoropropyldimethicone; and silicone elastomers, for instance the products sold under the names "KSG" by the company Shin-Etsu, under the names "Trefil", "BY29" or "EPSX" by the company Dow Corning or under the names "Gransil" by the company Grant Industries.

These fatty substances may be chosen in a varied manner by a person skilled in the art in order to prepare a composition having the desired properties, for example consistency or texture properties.

When it is present, the amount of oily phase may range, for example, from 0.01% to 50% by weight and preferably from 0.1% to 30% by weight relative to the total weight of the composition.

The emulsions and foaming compositions of the invention may also contain adjuvants commonly used in cosmetics and dermatology, such as mineral or organic fillers, hydrophilic or lipophilic active agents, preserving agents, gelling agents, plasticizers, antioxidants, fragrances, odour absorbers, UV screening agents, sequestering agents (EDTA), acidic or basic pH regulators or buffers, and dyestuffs (pigments or colorants or nacres). In the case of emulsions, these adjuvants, depending on their nature, may be introduced into the oily phase, into the aqueous phase and/or into lipid vesicles. The amounts of these various additives are those conventionally used in the fields under consideration, for example, from 0.01 to 20% of the total weight of the composition. Needless to say, a person skilled in the art will take care to select the optional compound(s) to be added to the foaming compositions and emulsions according to the invention such that the advantageous properties intrinsically associated with these compositions are not, or are not substantially, adversely affected by the envisaged addition.

The term "fillers" should be understood as meaning colourless or white, mineral or synthetic, lamellar or non-lamellar particles intended to give body or rigidity to the composition and/or softness, a matt effect and uniformity to make-up. Fillers that may especially be mentioned are talc, mica, silica, boron nitride, bismuth oxychloride, kaolin, Nylon powders such as Nylon-12 (Orgasol sold by the company Atochem), polyethylene powders, Teflon (tetrafluoroethylene polymer powders), polyurethane powders, polystyrene powders, polyester powders, optionally modified starch, copolymer microspheres, such as those sold under the name Expancel by the company Nobel Industrie, microsponges, for instance Polytrap sold by the company Dow Corning, silicone resin microbeads such as those sold by the company Toshiba under the name Tospearl, precipitated calcium carbonate, magnesium carbonate, magnesium hydrocarbonate, hydroxyapatite, hollow silica microspheres (Silica Beads from the company Maprecos), glass or ceramic microcapsules, metal soaps derived from organic carboxylic acids containing from 8 to 22 carbon atoms and preferably from 12 to 18 carbon atoms, for example zinc, magnesium or lithium stearate, zinc laurate or magnesium myristate, and mixtures thereof.

The term "pigments" should be understood as meaning white or coloured, mineral or organic particles, insoluble in the medium, that are intended to colour and/or opacify the composition. They may be white or coloured, mineral and/or organic, and of standard or nanometric size. Among the mineral pigments and nanopigments that may be mentioned are titanium dioxide, zirconium dioxide or cerium dioxide, and also zinc oxide, iron oxide or chromium oxide, nanotitaniums (titanium dioxide nanopigments), nanozincs (zinc oxide nanopigments) and ferric blue. Among the organic pigments that may be mentioned are carbon black and lakes, for instance calcium, barium, aluminium or zirconium salts, of acidic dyes such as halo acid dyes, azo dyes or anthraquinone dyes.

The term "nacres" should be understood as meaning iridescent particles that reflect light. Among the nacres that may be envisaged, mention may be made of natural mother-of-pearl, mica coated with titanium oxide, with iron oxide, with natural pigment or with bismuth oxychloride, and also coloured titanium mica.

In the case of the emulsions, a gelling agent may in particular be added thereto so as to adjust the texture of the emulsion and to gain access to a wide range of textures from a milk to a cream.

The gelling agents that may be used may be hydrophilic gelling agents. Examples of hydrophilic gelling agents that may be mentioned in particular are carboxyvinyl polymers (carbomer), acrylic copolymers such as acrylate/alkylacrylate copolymers, polyacrylamides, polysaccharides, natural gums and clays.

The foaming compositions and emulsions of the invention may especially be in the form of a cosmetic, make-up, cleansing or care composition, which may be applied to the skin, including the scalp, the nails, the hair, the eyelashes, the eyebrows, the eyes, mucous membranes and semi-mucous membranes, and any other area of body or facial skin.

As a product for cleansing and/or removing make-up from the skin (of the body or the face), the foaming compositions according to the invention may be used in two ways:

the first use consists in spreading the gel in the hands, applying it to the face or the body and then massaging it in the presence of water to develop the foam directly on the face or the body, the other possible use of this type of product consists in developing the foam in the palms of the hands before applying it to the face or the body.

If the composition is sufficiently fluid, it may be packaged in a self-foaming aerosol or air spray bottle. The product is then delivered in the form of a foam which is applied directly to the skin or the hair.

In all cases, the foam is then rinsed off.

Another subject of the invention consists of a cosmetic process for cleansing and/or removing make-up from the skin, the scalp and/or the hair, characterized in that the composition of the invention is applied to the skin, to the scalp and/or to the hair, in the presence of water, and the foam formed and the soiling residues are removed by rinsing with water.

The emulsions according to the invention may be used in many cosmetic or dermatological applications, especially for treating, caring for and/or making up facial skin and/or body skin, mucous membranes (lips), the scalp and/or keratin fibres (hair or eyelashes), and/or to protect the skin against UV rays.

Thus, a subject of the present invention is the cosmetic use of the cosmetic emulsion as defined above, for treating, caring for, protecting and/or making up facial skin and/or body skin, mucous membranes, the scalp and/or keratin fibres.

Other characteristics and advantages of the invention will emerge more clearly on reading the description which follows, given by way of non-limiting illustration.

DETAILED DESCRIPTION OF EMBODIMENTS

The examples that follow illustrate the use of polymers comprising water-soluble units and units with an LCST to prepare foaming compositions and emulsions.

The polymers used in these examples consist of a polyacrylic acid (PAA) backbone bearing side chains or grafts consisting of units with an LCST. They are characterized by the molar mass of the water-soluble backbone (polyacrylic acid), the chemical nature of the chains with an LCST, their proportion by mass in the polymer and their molar mass. The characteristics of the polymers used are given in Table 1.

TABLE 1

|  | Water-soluble backbone | Grafts (units with an LCST) | Proportion: units with an LCST in the final polymer (by weight) | Degree of grafting (mol %) |
|---|---|---|---|---|
| Polymer 1 | Polyacrylic acid; MW = 450 000 | $(EO)_6(PO)_{39}$ random Jeffamine M-2005; MW = 2600 | 51% | 3.9% |
| Polymer 2 | Polyacrylic acid; MW = 550 000 | Poly-N-isopropylacrylamide (pNIPAM) MW = 10 000 | 49% | 0.9% |
| Polymer 3 | Polyacrylic acid; MW = 750 000 | $(EO)_6(PO)_{39}$ random Jeffamine M-2005; MW = 2600 | 45% | 3.1% |

These polymers are prepared in the following manner.

Preparation of polymer 1

3 grams of polyacrylic acid with an average molar mass of 450 000 g/mol (Aldrich) are dissolved in 220 ml of N-methylpyrrolidone in a 500 ml reactor equipped with a condenser, with stirring at 60° C. for 12 hours. 4.181 grams of monoamino random $(EO)_6(PO)_{39}$ copolymer with a molar mass of 2600 g/mol having a cloud point, at a concentration of 1% by weight in water, of 16° C. (Jeffamine M-2005 from Huntsman) are dissolved in 50 ml of N-methylpyrrolidone with stirring, at 20° C., for 15 minutes. The solution obtained is added dropwise to the reaction medium containing the polyacrylic acid, with vigorous stirring at 60° C.

2.158 grams of dicyclohexylcarbodiimide are dissolved in 30 ml of N-methylpyrrolidone with stirring at 20° C. for 15 minutes. The solution obtained is added dropwise to the reaction medium containing the polyacrylic acid and the monoamino random $(EO)_6(PO)_{39}$ copolymer, with vigorous stirring at 60° C. The final mixture is stirred for 12 hours at 60° C.

The mixture is cooled to 20° C. and is then placed in a refrigerator at 4° C. for 24 hours. The crystals of dicyclohexylurea formed are removed by filtration of the reaction medium.

The polymer is then neutralized with 19 g of 35% sodium hydroxide (4-fold excess relative to the number of moles of acrylic acid), leading, to its precipitation. After standing for 12 hours, the reaction medium is filtered so as to recover the precipitated polymer. This polymer is dried under vacuum at 35° C. for 24 hours.

13.55 grams of solid are recovered and are dissolved in 2 litres of deionized water. This solution is ultrafiltered using a Millipore ultrafiltration system containing a membrane with a cutoff threshold set at 10 000 daltons. The solution thus purified is freeze-dried so as to collected the polymer in solid form.

7.05 grams of polyacrylic acid (450 000 g/mol) grafted with 3.9% (on a molar basis) of monoamino random $(EO)_6(PO)_{39}$ copolymer are obtained.

The proportion by mass of the units with an LCST in the final polymer is 51%.

The polymer thus obtained has a solubility in water, at 20° C., of at least 10 g/l.

Preparation of Polymer 2

Polymer 2, which comprises poly-N-isopropylacrylamide (pNIPAM) grafts, is prepared by a 2-step process:

1) Synthesis of the pNIPAM oligomers bearing a reactive amino end group.

8 grams of N-isopropylacrylamide and 80 ml of dimethyl sulphoxide are introduced into a 250 ml three-necked round-bottomed flask equipped with a condenser and a nitrogen inlet. This mixture is heated with stirring to 29° C. using a water bath and nitrogen is bubbled through. After 45 minutes, 0.161 gram of aminoethanethiol hydrochloride predissolved in 4 ml of dimethyl sulphoxide is added to the reaction medium. 5 minutes later, 0.191 gram of potassium persulphate dissolved in 8 ml of dimethyl sulphoxide is added to the reaction medium. This reaction medium is stirred under a nitrogen atmosphere for 3 hours at 29° C.

The poly-N-isopropylacrylamide (pNIPAM) oligomers synthesized are isolated by precipitation from the reaction medium in a mixture of acetone (40% by volume) and hexane (60%).

2) Grafting of the pNIPAM Oligomers onto Polyacrylic Acid 3 grams of polyacrylic acid with a molar mass of 550 000 g/mol are dissolved in 100 ml of 1-methyl-2-pyrrolidone in a 250 ml three-necked round-bottomed flask, with stirring at 60° C. for 12 hours. 3.757 grams of PNIPAM oligomers predissolved in 25 ml of 1-methyl-2-pyrrolidone are introduced dropwise into the reaction medium with stirring. 15 minutes later, 0.776 gram of dicyclohexylcarbodiimide predissolved in 25 ml of 1-methyl-2-pyrrolidone is introduced dropwise into the reaction medium with vigorous stirring. The reaction medium is maintained at 60° C. for 12 hours with stirring.

The reaction medium is then cooled to 20° C. and then placed in a refrigerator at 4° C. for 24 hours. The dicyclohexylurea crystals formed are then removed by filtration. The polymer is then neutralized using 19 g of 35% sodium hydroxide (4-fold excess relative to the number of moles of acrylic acid), leading to its precipitation. After standing for 12 hours, the reaction medium is filtered so as to recover the precipitated polymer. This polymer is dried under vacuum at 35° C. for 24 hours.

10.2 grams of solid are recovered and are dissolved in 2 litres of deionized water. This solution is ultrafiltered using a Millipore ultrafiltration system containing a membrane with a cutoff threshold set at 10 000 daltons. The solution thus purified is freeze-dried so as to collect the polymer in solid form.

4.8 grams of polyacrylic acid (550 000 g/mol) grafted with 0.9% (on a molar basis) of poly-N-isopropylacrylamide are obtained.

The proportion by mass of the units with an LCST in the final polymer is 49%.

Preparation of Polymer 3

1.51 grams of polyacrylic acid with an average molar mass of 750 000 g/mol (Aldrich) are dissolved in 350 ml of deionized water in a 1 litre reactor equipped with a condenser, with stirring at 20° C. for 12 hours. The pH of the reaction medium is then adjusted to 8 with a 1M sodium hydroxide solution. 1.60 grams of monoamino random $(EO)_6(PO)_{39}$ copolymer (Jeffamine M-2005 from Huntsman) are dissolved in 100 ml of deionized water with stirring at 5° C. for 30 minutes. The solution obtained is added dropwise to the reaction medium with vigorous stirring.

1.84 grams of 1-(3-dimethylaminopropyl)-3-ethylcarbodiimide hydrochloride are dissolved in 50 ml of deionized water with stirring at 20° C. for 15 minutes. The solution obtained is added dropwise, with vigorous stirring, to the above reaction medium, which is then heated at 60° C. for 6 hours.

The reaction medium is cooled to 20° C. and then concentrated and precipitated from acetone. The polymer in solid form is recovered by filtration and washed with an excess of acetone. The powder is ground and dried under vacuum at 35° C.

3.33 g of polyacrylic acid (750 000 g/mol) grafted with 3.1% (on a molar basis) of monoamino random $(EO)_6(PO)_{39}$ copolymer are obtained (94% yield).

The demixing temperatures of the units with an LCST of the polymers, that is to say of the Jeffamine units and of the pNIPAM units, are determined.

These demixing temperatures are determined by visible UV spectroscopy by measuring, at a wavelength equal to 500 nm, the transmittance of aqueous solutions of these units as a function of temperature; the demixing temperature is identified at the temperature beyond which the transmittance becomes 10% less than its value at 10° C. The results obtained for various concentrations by mass are collated in Table 2 below:

TABLE 2

| Concentration by mass in aqueous solution (%) | Random $(EO)_6(PO)_{39}$ Jeffamine M-2005; MW = 2600 | Poly-N-isopropyl-acrylamide pNIPAM MW = 10 000 |
|---|---|---|
| 0.025 | 37° C. | 37° C. |
| 0.05 | 36° C. | 36° C. |
| 0.15 | / | 32° C. |
| 1 | 16° C. | 32° C. |

In the above examples, the viscosity measurements were performed using a Haake RS150 rheometer equipped with a cone/plate geometry (35 mm, 2°) and a thermostatic bath so as to maintain the temperature between 5 and 80° C. The measurements were carried out in the flow mode, at an imposed shear rate equal to $10 \, s^{-1}$, by varying the temperature from 20 to 40° C. at a rate of 0.5° C./min.

EXAMPLE 1

Surface activity of polymers 1 and 2 comprising a water-soluble backbone and grafts consisting of units with an LCST The surface tensions (σ) were measured using a ring tensiometer (tensiometer K12 from Kruss), equipped with a thermostatic bath for maintaining the temperature between 5° C. and 80° C. The polymer solutions were prepared by simple dissolution with stirring of the appropriate amount of polymer in powder form in water, at room temperature, to obtain a polymer concentration of 0.05 or 0.1% by mass.

The measurements were performed at two temperatures:

15° C., value below the mixing temperature of the grafts with an LCST (polymers 1 and 2) at concentrations of 0.05 and 0.1%, 38° C., value above the demixing temperature of the grafts with an LCST (polymers 1 and 2) at these concentrations.

The results are given in Table 3.

TABLE 3

| | Water | Polymer 1 | Polymer 2 | PAA backbone | Grafts of polymer 1 | Grafts of polymer 2 |
|---|---|---|---|---|---|---|
| σ (water) mN/m at 15° C. | 73.5 | / | / | / | / | / |
| σ (water) mN/m at 38° C. | 6.95 | / | / | / | / | / |
| σ (0.05%) mN/m at 15° C. | / | 45 | 44 | 55 | 41 | 35 |
| σ (0.05%) mN/m at 38° C. | / | 36 | 38 | 51 | Not measurable since insoluble | Not measurable since insoluble |
| σ (0.1%) mN/m at 15° C. | / | 45 | 42 | / | / | / |
| σ (0.1%) mN/m at 38° C. | / | 35 | 36 | / | / | / |

The concentrations are given as percentages by mass.

The results of Table 3 show that a significant reduction in the surface tension of water is obtained with polymers 1 and 2, this reduction being even greater above the demixing temperature.

EXAMPLE 2

Foaming Formula Composed of Polymer 3 at a Concentration of 0.3% by Mass, T=25° C.

The foam is prepared from an aqueous solution of polymer 3 at 0.3% by mass (5 grams of solution in 10 ml pill bottles) subjected to stirring using a Diax 600 machine (Heidolph) for 5 minutes at 8000 rpm, and then for 1 minute at 13 500 rpm. The shaft used has an outside diameter of 10 mm (reference 10F).

For comparative purposes, foams are prepared in the same manner but using only a) the water-soluble backbone of polymer 3 in water, at a concentration of 0.15% by mass, and b) grafts with an LCST in water at a concentration of 0.15% by mass.

A change in the macroscopic appearance of the foams thus obtained is monitored over time; the foaming power is proportionately greater the greater the height of foam in the container.

In the case of polymer 3 at a concentration of 0.3% by mass, a substantial foam which is virtually unchanged after 1 hour is obtained; it destabilizes slightly after 3 days.

In the case of the water-soluble backbone of polymer 3, at a concentration of 0.15% by mass, the production of foam is very low, the foam destabilizes after 30 minutes and disappears completely after 3 days. In the case of the grafts of polymer 3 at a concentration of 0.15% by mass, a foam that disappears completely after 15 minutes is obtained.

Thus, polymer 3 has foaming properties superior to those of the water-soluble backbone and to those of the grafts with an LCST. Since the aqueous solutions of polymer 3 (at 0.3%) and of PAA backbone (at 0.15%) have the same viscosity (≈0.5 Pa.s for a shear rate of $10s^{-1}$), the improved stability of the foam obtained with polymer 3 compared with that containing the water-soluble backbone is not due to a thickening effect.

EXAMPLE 3

Foam formula composed of polymer 2 at a concentration of 0.1% by mass, T=15° C. and 38° C.

Foams are prepared using an aqueous solution of polymer 2 at 0.1% by mass (5 grams of solution in 10 ml pill bottles) subjected to stirring using a Diax 600 machine (Heidolph) for 5 minutes at 8000 rpm, and then for 1 minute at 13 500 rpm. The shaft used has an outside diameter of 10 mm (reference 10F).

Foams are prepared in the same way using an aqueous solution comprising 0.15% by mass of the water-soluble backbone of polymer 2 and of an aqueous solution of grafts with an LCST of polymer 2, at a concentration of 0.15% by mass.

The change in the macroscopic appearance of the foams thus obtained is monitored over time, at a temperature of 15° C. and of 38° C., in the case of polymer 2 and at a temperature of 25° C. in the case of the water-soluble backbone and of the grafts with an LCST.

In the case of polymer 2, a substantial foam is obtained at 15° C., but the foam height decreases after 30 minutes (50% less foam) and it disappears after 2 hours. At 38° C., a substantial foam is also obtained, which persists 2 hours later (40% foam remains) and which is still partially present after 22 hours (25% foam still remains).

In the case of the water-soluble backbone of polymer 2, a very low foam height is obtained at 25° C. and the foam disappears after 5 minutes. In the case of the grafts with an LCST, a substantial foam is obtained at 25° C., which destabilizes instantaneously (80% foam and 20% liquid) and then substantially after 30 minutes (only 15% foam remains), until it disappears after 2 hours.

Thus, polymer 2 has foaming properties that are superior to those of the water-soluble backbone and of the grafts with an LCST. This foaming power is observed over a wide range of temperatures and is improved when the temperature becomes higher than the demixing temperature of the chains with an LCST, which is 36° C., at a concentration of 0.15% by mass. This improvement in the foaming power of polymer 2 from 15° C. to 38° C. is not associated with a heat-induced gelling effect since the viscosities of polymer 2 in aqueous solution at 0.1% are as follows:

viscosity at 15° C. ($10\ s^{-1}$): 0.007 Pa.s;
viscosity at 38° C. ($10\ s^{-1}$): 0.005 Pa.s.

EXAMPLE 4

Water/Oil Interface Activity of Polymers 1 and 2 Comprising a Water-Soluble Backbone and Grafts with an LCST The interface tensions (σ) are measured using a drop profile tensiometer (Tensiometer G10 from Krüss), equipped with a thermostatic bath for maintaining the temperature between 5° C. and 80° C. The polymer solutions were prepared by simple dissolution with stirring of the appropriate amount of polymer in powder form in water, at room temperature to obtain polymer concentrations of 0.05% or 0.1% by mass. The measurements were performed at a water/Parleam oil interface, at two temperatures:

15° C., value below the demixing temperature of the grafts with an LCST (polymers 1 and 2),
38° C., value above the demixing temperature of the grafts with an LCST (polymers 1 and 2).

The results are given in Table 4.

TABLE 4

| | Water | Polymer 1 | Polymer 2 | PAA backbone | Grafts of polymer 1 | Grafts of polymer 2 |
|---|---|---|---|---|---|---|
| σ (water) mN/m at 15° C. | 40 | / | / | / | / | / |
| σ (water) mN/m at 38° C. | 39 | / | / | / | / | / |
| σ (0.05%) mN/m at 15° C. | / | / | / | 39 | 9 | 8 |
| σ (0.05%) mN/m at 38° C. | / | / | / | 38 | Not measurable since insoluble | Not measurable since insoluble |
| σ (0.1%) mN/m at 15° C. | / | 15 | 18 | / | / | / |
| σ (0.1%) mN/m at 38° C. | / | 10 | 15 | / | / | / |

The concentrations are given as percentages by mass in the aqueous phase.

The results of Table 4 show that the water interface tension in the presence of polymers 1 and 2 is decreased by 25 or 22 mM/m at 15° C. and by 29 to 24 mM/m at 38° C. in the case of solutions of polymers 1 and 2 at 0.1% by mass.

EXAMPLE 5

Emulsion Containing Polymer 3 at a Concentration of 0.3% by Mass in the Aqueous Phase, T=25° C.

The emulsion is prepared using an aqueous solution of polymer 3 at 0.3% by mass (4.8 g) and of Parleam oil (1.2 g), and the mixture is subjected to stirring using a Diax 600 machine (Heidolph) for 5 minutes at 8000 rpm, and then for 1 minute at 13 500 rpm. The shaft used has an outside diameter of 10 mm (reference F10). The emulsification is performed in pill bottles with a volume of 10 ml. The fraction by mass of Parleam oil was set at 20%.

Emulsions are prepared in the same way using an aqueous solution of the water-soluble backbone of polymer 3 at a concentration of 0.15% by mass, and an aqueous solution of the grafts with an LCST of polymer 3 at a concentration of 0.15% by mass.

The change in the macroscopic appearance of the emulsions is monitored over time; the emulsifying power is proportionately greater the greater the height of the emulsified phase.

In the case of polymer 3 at 0.3% by mass, at 25° C., the whole composition is emulsified and remains stable for 64 days. In the case of the water-soluble backbone of polymer 3 at 0.15% by mass, a good emulsion height is obtained, but it decreases after 64 days.

In the case of the grafts with an LCST of polymer 3, a lower emulsion height is obtained, and the emulsion disappears after 52 hours.

Thus, polymer 3 has emulsifying properties that are superior to those of the water-soluble backbone and of the grafts with an LCST. Since the aqueous solutions of polymer 3 (at 0.3%) and of PAA backbone (at 0.15) have the same viscosity ($\approx$0.5 Pa.s for a shear rate of 10 s$^{-1}$), the improved stability of the emulsion obtained with polymer 3 compared with that containing the water-soluble backbone is not due to a thickening effect.

EXAMPLE 6

Emulsions Containing Polymer 2, at a concentration in the aqueous phase of 0.3% (by mass), T=15° C. and 38° C.

The emulsions are prepared from an aqueous solution of polymer 3 at 0.3% by mass (4.8 g) and of Parleam oil (1.2 g); the mixture is subjected to stirring using a Diax 600 machine (Heidolph) for 5 minutes at 8000 rpm, and then for 1 minute at 13 500 rpm. The shaft used has an outside diameter of 10 mm (reference 10F). The emulsification is performed in pill bottles with a volume of 10 ml. The mass fraction of Parleam oil was set at 20%.

The change in the macroscopic appearance of the emulsions is monitored over time; the emulsifying power is proportionately greater the greater the height of emulsified phase.

At 15° C., the whole volume is initially emulsified for polymer 2 and half the height of the emulsified phase disappears after 63 days.

At 38° C., the emulsion obtained with polymer 2 is also very substantial, and it remains stable for 63 days.

Thus, polymer 2 has emulsifying properties over a wide range of temperatures and its emulsifying power is improved when the temperature becomes higher than the demixing temperature of the chains with an LCST (32° C. for a concentration of 0.3%). This improvement is not associated with a heat-induced gelling effect since the viscosities of polymer 2 in aqueous solution at 3% are as follows:

viscosity at 15° C. (10 s$^{-1}$): 0.12 Pa.s;
viscosity at 38° C. (10 s$^{-1}$): 0.12 Pa.s.

Examples of cosmetic compositions in emulsion or foam form are described below.

EXAMPLE 7

Fluid Foaming Composition

| | |
|---|---|
| Glycerol | 5% by weight |
| Polymer 3 | 0.3% by weight |
| Preserving agent | 0.4% by weight |
| Sodium ethylenediaminetetraacetate | 0.2% by weight |
| Demineralized water | 94.1% by weight |

This foaming composition is obtained by dissolving polymer 3 in powder form in demineralized water with stirring at room temperature for 3 hours; the other constituents are then introduced into this solution and stirring is continued for 30 minutes.

The formula obtained is a fluid foaming composition that can be used from 5° C. to 60° C.

EXAMPLE 8

Body Milk

This milk contains an oily phase and an aqueous phase having the following compositions:

| | |
|---|---|
| Oily phase | |
| Parleam oil | 9% by weight of the milk |
| Cyclodimethylsiloxane | 6% by weight of the milk |
| Aqueous phase | |
| Polymer 3 | 0.3% by weight of the milk |
| Preserving agent | 0.2% by weight of the milk |
| Demineralized water | 84.5% by weight of the milk |

The aqueous phase is obtained by dissolving polymer 3 in powder form and the preserving agent in demineralized water with stirring for 3 hours. The oil phase is then introduced slowly into the aqueous phase with stirring using a Moritz blender at a speed of 4000 rpm for 20 minutes.

The formula obtained is an emulsion with a beautiful, fluid and aqueous texture.

REFERENCES

[1] D. Hourdet et al., Polymer, 1994, Vol. 35, No. 12, pages 2624-2630;
[2] F. L'Alloret et al., Coll. Polym. Sci., 1995, Vol. 273, No. 12, pages 1163-1173;
[3] F. L'Alloret, Revue de l'Institut Francais du Pétrole [Review of the French Petroleum Institute], 1997, Vol. 52, No. 2, pages 117-128;
[4] EP-A-0 583 814;
[5] EP-A-0 629 649;
[6] WO-A-95/24430;
[7] U.S. Pat. No. 5,939,485,
[8] WO-A-97/00275,
[9] WO-A-98/48768,
[10] WO-A-00/35961
[11] EP-A-566 438
[12] FR-A-2 739 556

The invention claimed is:

1. A method of lowering the surface tension or the interface tension of water of a cosmetic composition comprising at least one cosmetic or dermatological adjuvant, the method comprising adding a polymer comprising water-soluble units and units with an LCST, the units with an LCST having in water a demixing temperature of from 5 to 40° C. at a concentration of 1% by mass in water and wherein the water-soluble units are different than the units with an LCST, to water in an amount sufficient to lower the surface tension or the interface tension of water, wherein the polymer comprises an oligomer or copolymer of water-soluble units, wherein the polymer is water-soluble in the entire range of 5 to 80° C. at a concentration of at least 10 g/l wherein the units with an LCST are-one or more of the following polymers:

polyethers; polyvinyl methyl ethers; polymeric N-substituted acrylamide derivatives;

copolymers of N-isopropylacrylamide or of N-ethylacrylamide and a vinyl monomer corresponding to formula (I):

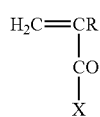

wherein:

R is from H, —CH$_3$, —C$_2$H$_5$ or —C$_3$H$_7$, and

X is:

OR' alkyl oxides wherein R' is a linear or branched, saturated or unsaturated hydrocarbon radical containing from 1 to 6 carbon atoms, optionally substituted with at least one halogen atom; a sulphonic group, a sulphate group, a phosphate group; a hydroxyl group; a primary amine; a secondary amine; a tertiary amine; or a quaternary amine group of the formula N$^+$R$_1$R$_2$R$_3$ wherein R$_1$, R$_2$ and R$_3$ are, independently, a linear or branched, saturated or unsaturated hydrocarbon radical containing 1 to 6 carbon atoms, with the proviso that the sum of the carbon atoms of R'+R$_1$ +R$_2$ +R$_3$ does not exceed 7; and —NH$_2$, —NHR$_4$ and —NR$_4$R$_5$ groups in which R$_4$ and R$_5$ are, independently of each other, linear or branched, saturated or unsaturated hydrocarbon radicals containing 1 to 6 carbon atoms, with the proviso that the total number of carbon atoms in R$_4$ +R$_5$ does not exceed 7, the said R$_4$ and R$_5$ optionally being substituted with a halogen atom (iodine, bromine, chlorine or fluorine); a hydroxyl (—OH); sulphonic (—SO$_3^-$), sulphate (—SO$_4^-$); phosphate (—PO$_4$H$_2$); primary amine (—NH$_2$); secondary amine (—NHR$_1$), tertiary amine (—NR$_1$R$_2$) and/or quaternary amine (—N$^{+R}_1$R$_2$R$_3$) group with R$_1$, R$_2$ and R$_3$ being, independently of each other, a linear or branched, saturated or unsaturated hydrocarbon radical containing 1 to 6 carbon atoms, with the proviso that the sum of the carbon atoms of R$_4$+R$_5$+R$_1$ +R$_2$ +R$_3$ does not exceed 7;

copolymers of N-isopropylacrylamide or of N-ethylacrylamide and a monomer selected from the group consisting of maleic anhydride, itaconic acid, vinylpyrrolidone, styrene and its derivatives, dimethyldiallylammonium chloride, vinylacetamide, vinyl ethers and vinyl acetate derivatives; or polyvinylcaprolactam; copolymers of vinylcaprolactam and a vinyl monomer corresponding to formula (I).

2. The method as claimed in claim 1, in which the lowering of the surface tension or of the interface tension of water is at least 15 mN/m for a concentration of polymer in water of 0.1% by mass in the temperature range from 5 to 80° C.

3. The method as claimed in claim 1, in which the lowering of the surface tension or of the interface tension of water is of at least 20 mN/in for a concentration of polymer in water of 0.1% by mass when the temperature is higher than the demixing temperature of the units with an LCST at this concentration.

4. The method as claimed in claim 1, wherein the polymer is in the form of a block polymer comprising water-soluble units alternating with units with an LCST, or in the form of a grafted polymer whose backbone is formed from water-soluble units and which bears grafts consisting of units with an LCST or a grafted polymer whose backbone is formed from units with an LCST and which bears grafts consisting of water-soluble units.

5. The method as claimed in claim 1, wherein the water-soluble units are obtained by free-radical polymerization of at least one monomer selected from the group consisting of:

(meth)acrylic acid;

vinyl monomers of formula (I) below:

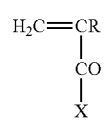

wherein:

R is from H, —CH$_3$, —C$_2$H$_5$ or —C$_3$H$_7$, and

X is:

OR' alkyl oxides wherein R' is a linear or branched, saturated or unsaturated hydrocarbon radical containing from 1 to 6 carbon atoms, optionally substituted with at least one halogen atom; a sulphonic group, a sulphate group, a phosphate group; a hydroxyl group; a primary amine; a secondary amine; a tertiary amine; or a quaternary amine group of the formula N$^+$R$_1$R$_2$R$_3$ wherein R$_1$, R$_2$ and R$_3$ are, independently, a linear or branched, saturated or unsaturated hydrocarbon radical containing 1 to 6 carbon atoms, with the proviso that the sum of the carbon atoms of R' +R$_1$ +R$_2$ +R$_3$ does not exceed 7; and —NH$_2$, —NHR$_4$ and —NR$_4$R$_5$ groups in which R$_4$ and R$_5$ are, independently of each other, linear or branched, saturated or unsaturated hydrocarbon radicals containing 1 to 6 carbon atoms, with the proviso that the total number of carbon atoms in R$_4$ +R$_5$ does not exceed 7, the said R$_4$ and R$_5$ optionally being substituted with a halogen atom (iodine, bromine, chlorine or fluorine); a hydroxyl (—OH); sulphonic (—SO$_3^-$), sulphate (—SO$_4^-$); phosphate (—PO$_4$H$_2$); primary amine (—NH$_2$); secondary amine (—NHR$_1$), tertiary amine (—NR$_1$R$_2$) and/or quaternary amine (—N$^{+R}_1$R$_2$R$_3$) group with R$_1$, R$_2$and R$_3$ being, independently of each other, a linear or branched, saturated or unsaturated hydrocarbon radical containing 1 to 6 carbon atoms, with the proviso that the sum of the carbon atoms of R$_4$+R$_5$+R$_1$ +R$_2$ +R$_3$ does not exceed 7;

maleic anhydride;

itaconic acid;

vinyl alcohol of formula CH$_2$=CHOH;

vinyl acetate of formula CH$_2$=CH—OCOCH$_3$;

N-vinyllactams such as N-vinylpyrrolidone, N-vinylcaprolactam and N-butyrolactam;

vinyl ethers of formula CH$_2$=CHOR$_6$ in which R$_6$ is a linear or branched, saturated or unsaturated hydrocarbon radical containing from 1 to 6 carbon atoms;

water-soluble styrene derivatives, especially styrene sulphonate;

dimethyldiallylammonium chloride; and vinylacetamide.

6. The method as claimed in claim 1, wherein the water-soluble units have a molar mass ranging from 1000 g/mol to 5 000 000 g/mol when they constitute the water-soluble backbone of a grafted polymer, or a molar mass ranging from 500 g/mol to 100 000 g/mol when they constitute one block of a multiblock polymer or when they constitute the grafts of a grafted polymer.

7. The method as claimed in claim 1, wherein the molar mass of the units with an LCST is from 500 to 5300 g/mol.

8. The method as claimed in claim 7, wherein the molar mass of the units with an LCST is from 1500 to 4000 g/mol.

9. The method as claimed in claim 1, wherein the units with an LCST comprise
a polyvinylcaprolactam;
a copolymer of vinylcaprolactam and of a vinyl monomer corresponding to formula (I):

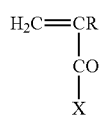

wherein:
R is from H, —CH$_3$, —C$_2$H$_5$ or —C$_3$H$_7$, and
X is:
OR' alkyl oxides wherein R' is a linear or branched, saturated or unsaturated hydrocarbon radical containing from 1 to 6 carbon atoms, optionally substituted with at least one halogen atom; a sulphonic group, a sulphate group, a phosphate group; a hydroxyl group; a primary amine; a secondary amine; a tertiary amine; or a quaternary amine group of the formula N$^+$R$_1$R$_2$R$_3$ wherein R$_1$, R$_2$ and R$_3$ are, independently, a linear or branched, saturated or unsaturated hydrocarbon radical containing 1 to 6 carbon atoms, with the proviso that the sum of the carbon atoms of R' +R$_1$ +R$_2$ +R$_3$ does not exceed 7; or
a monomer selected from the group consisting of maleic anhydride, itaconic acid, vinylpyrrolidone, styrene; styrene derivatives, dimethyldiallylammonium chloride, vinylacetamide, vinyl alcohol, vinyl acetate, vinyl ethers, and vinyl acetate derivatives.

10. The method as claimed in claim 1, wherein the proportion by mass of the units with an LCST is from 5 to 70% relative to the polymer.

11. The method as claimed in claim 10, wherein the proportion by mass of the units with an LCST is from 20 to 65% relative to the polymer.

12. The method as claimed in claim 10, wherein the proportion by mass of the units with an LCST is from 30 to 60% relative to the polymer.

13. The method as claimed in claim 1, wherein the concentration by mass of the polymer in the aqueous phase is less than or equal to 5%.

14. The method as claimed in claim 13, wherein the concentration by mass of the polymer in the aqueous phase is from 0.01% to 5%.

* * * * *